(12) United States Patent
Yeo

(10) Patent No.: US 8,506,973 B2
(45) Date of Patent: Aug. 13, 2013

(54) INJECTABLE ANTICANCER COMPOSITION FOR LOCAL ADMINISTRATION CONTAINING HYDROXYCHLOROQUINE

(76) Inventor: Oh-Young Yeo, Goyang-si (KR)

(*) Notice: Subject to any disclaimer, the term of this patent is extended or adjusted under 35 U.S.C. 154(b) by 0 days.

(21) Appl. No.: 13/380,042

(22) PCT Filed: Jun. 18, 2010

(86) PCT No.: PCT/KR2010/003938
§ 371 (c)(1),
(2), (4) Date: Dec. 22, 2011

(87) PCT Pub. No.: WO2010/151005
PCT Pub. Date: Dec. 29, 2010

(65) Prior Publication Data
US 2012/0095045 A1    Apr. 19, 2012

(30) Foreign Application Priority Data
Jun. 24, 2009  (KR) .................. 10-2009-0056251

(51) Int. Cl.
*A61K 9/00* (2006.01)
*A61K 9/14* (2006.01)

(52) U.S. Cl.
USPC .................... 424/400; 424/93; 424/72; 435/2

(58) Field of Classification Search
USPC ................... 424/400; 977/773, 906
See application file for complete search history.

(56) References Cited

U.S. PATENT DOCUMENTS
2008/0279851 A1* 11/2008 Coyle et al. ............... 424/133.1

FOREIGN PATENT DOCUMENTS
KR          100390332 B1      7/2003
WO      WO 02/13826 A1 *     2/2002

OTHER PUBLICATIONS

Dai, et al., "Effect of Yangyin Humo Decoction on oral mucomembranous reaction to radiotherapy", Chin J Integr Med. Aug. 2009;15(4):303-6. Epub Aug. 18, 2009 by NCBI.*
Toyosaki, T.; "Antioxidant effect of riboflavin in enzymic lipid peroxidation", J. Agric. Food Chem., 1992, 40 (10), pp. 1727-1730, published by ACS.*
Martirosyan, A. R. et al., Differentiation-inducing quinolines as experimental breast cancer agents in the MCF-7 human breast cancer cell model. Biochemical Pharmacology, 2004, vol. 68, pp. 1729-1738, ISSN:0006-2952. See abstract, results and drawing.
Strobl, J. S. et al., Distinct N-terminal histone H3/H4 modifications during MCF-7 mammary tumor cell differentiation by all-trans retinoic acid and hydroxychloroquine. Proc. Amer. Assoc. Cancer Res, vol. 46, 2005, Cellular and Molecular Biology 36: Epigenetic Mechanisms 1, Abstract #2745. See abstract.
Lagneaux, L. et al., Hydroxychloroquine-induced apoptosis of chronic lymphocytic leukemia involves activation of caspase-3 and modulation of Bc1-2/bax/ratio. Leuk Lymphoma, 2002, 43(5), pp. 1087-1095. See abstract.
Boya, P. et al., Mitochondrial membrane permeabilization is a critical step of lysosome-initiated apoptosis induced by hydroxychloroquine. Oncogene, 2003, vol. 22, pp. 3927-3936, ISSN:0950-9232. See abstract, concluding remarks.
Lagneaux, L. et al., Early induction of apoptosis in B-chronic lymphocytic leukaemia cells by hydroxychloroquine: activation of caspase-3 and no protection by survival factors. British Journal of Haematology, 2001, vol. 112, pp. 344-352, ISSN: 1365-2141.

* cited by examiner

*Primary Examiner* — Janet Epps-Smith
*Assistant Examiner* — Yanzhi Zhang
(74) *Attorney, Agent, or Firm* — Sherr & Jiang, PLLC

(57) ABSTRACT

The present invention relates to an injectable anticancer composition for local administration comprising hydroxychloroquine. The anticancer composition shows an $IC_{50}$ value against sarcoma-180 cells, which is about 10 times lower than cisplatin, as determined by the MTT assay in vitro, suggesting that the anticancer composition has an excellent cytotoxic effect. Also, the anticancer composition shows dose-dependent effects against solid cancer induced by sarcoma-80 cells in vivo. In addition, the anticancer composition has the effect of extending the life expectancy of patients having ascites cancer induced by sarcoma-80 cells.

11 Claims, 2 Drawing Sheets

INJECTABLE ANTICANCER COMPOSITION FOR LOCAL ADMINISTRATION CONTAINING HYDROXYCHLOROQUINE

BACKGROUND OF THE INVENTION

1. Technical Field

The present invention relates to an injectable composition for local administration comprising hydroxychloroquine as an active ingredient, in which the composition is to be injected directly into cancer cells to exhibit anticancer effects.

2. Description of the Related Art

Generally, tumors are diseases in which abnormal cells continuously proliferate to interfere with the function of normal cells. Tumors are classified according to histopathological and clinical criteria into malignant tumors and benign tumors, and the so-called cancer belongs to malignant tumors.

Cancer is the first leading cause of death in Korea and is also a leading cause of death worldwide. The cause of development of cancer or a method for treatment of cancer has not yet been elucidated. Cancer therapeutic agents that have been developed to date show problems associated with fatal side effects, expression of drug resistance, destruction of lymphocytes and bone marrow, etc., when they are clinically used. Thus, there is an urgent need to develop novel anticancer agents that exhibit cytoxic activity without influencing normal cells.

Up to now, about 270 kinds of cancer have been found to occur in the human body. Cell lines reported to be used in research of these kinds of cancer include Sarcoma-180 cells, melanoma cells, adenoma cells, adeno-carcinoma cells, Ehrlich ascites tumor cells and Walker carcinoma cells. Among these cells, Sarcoma-180 is a tumor cell line derived from an axillary carcinoma of a White male mouse, and it is known that Sarcoma-180 can be subcultured in ascites to exist in both the solid and ascites forms and has no species specificity when it is transplanted.

Meanwhile, hydroxychloroquine is currently being used for the prevention and treatment of rheumatoid arthritis, discoid and systemic lupus erythematosus, photosensitive skin diseases, and malaria. Recently, studies on hydroxychloroquine for the suppression of renal injury and the safe resection of glioma have been reported.

Korean Patent Registration No. 10-0390332 discloses an anticancer composition which allows an anticancer agent such as doxorubicin or cisplatin to be co-administered with hydroxychloroquine, chloroquine, primaquine or the like, which is frequently used as an anti-malaria agent, thereby reducing the 50% inhibitory concentration ($IC_{50}$) of the anticancer agent and inhibiting the drug resistance of cancer cells caused by the anticancer agent. Herein, the anti-malaria agent such as hydroxychloroquine is used as an adjuvant to inhibit the resistance of cancer cells against the anticancer agent so as to increase the anticancer effect of the anticancer agent, and the anticancer agent exhibits its effects by systemic administration via various routes such as oral and parenteral routes.

Until now, it has not been known that hydroxychloroquine has an anticancer effect. Thus, an anticancer agent based on hydroxychloroquine has not yet been reported.

BRIEF SUMMARY OF THE INVENTION

It is an object of the present invention to use hydroxychloroquine as an anticancer agent for local administration. Particularly, an object of the present invention is to provide an anticancer composition for local administration, which exhibits cytotoxic activity against cancer cells without influencing normal cells and is to be injected directly into cancer cells.

DETAILED DESCRIPTION OF THE INVENTION

Figure 1:
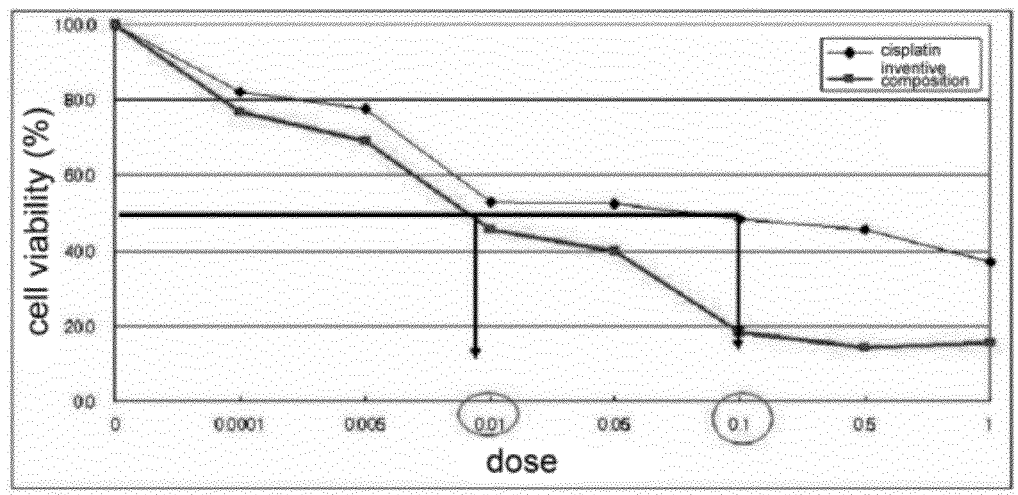
FIG. 1 is a graphic diagram showing the results of evaluating the effect of the composition of the present invention on the growth of the sarcoma-180 cell line in comparison with a control drug by an MTT assay.

In order to accomplish the above object, the present invention provides an injectable anticancer composition for local administration comprising hydroxychloroquine or its salt.

The anticancer composition of the present invention may be injected directly into cancer cells. Preferably, the anticancer composition of the present invention may further comprise a local anesthetic such as lidocaine and/or an antioxidant such as riboflavin.

The present invention aims to allow a composition based on hydroxychloroquine to be injected directly into cancer cells, thereby exhibiting anticancer effects. The composition for local administration containing hydroxychloroquine is administered directly into an affected local area to inactivate the local tissue, thereby blocking metabolism in the local tissue. The metabolism of cancer cells is faster than that of normal cells, and for this reason, when the metabolism of cancer cells is blocked by hydroxychloroquine, the cancer cell tissue will be inactivated, resulting in the necrosis of the cancer cell tissue.

The content of hydroxychloroquine in the composition of the present invention is preferably 5-25% (w/v), and preferably 20-25% (w/v). If the content of hydroxychloroquine is less than 5% (w/v), it will not exhibit therapeutic effects, and if the content of hydroxychloroquine is more than 25% (w/v), it can disadvantageously cause the necrosis of normal tissue surrounding cancer cells.

In the injectable composition for local administration according to the present invention, the local anesthetic serves to remove pain when the composition is administered by injection directly into cancer cells. As the local anesthetic, lidocaine is preferably used at a concentration of 1-2% (w/v). Also, the antioxidant serves to stabilize the composition. As the antioxidant, riboflavin is used at a concentration of 0.1-0.5% (w/v).

Also, in view of the solubility of hydroxychloroquine in water, a salt of hydroxychloroquine may be used. Particularly, a sulfate of hydroxychloroquine is preferred.

The injectable anticancer composition for local administration according to the present invention may be prepared according to any conventional method for preparing injectable formulations.

The injectable anticancer composition for local administration according to the present invention is preferably injected directly into cancer cells. The composition of the present invention may be repeatedly administered at intervals of 3-4 days for several weeks depending on the patient's conditions or may be repeatedly administered at intervals of 1-2 days depending on the size and progression of cancer cells, whereby it can inhibit the proliferation and metabolism of cancer cells to inactivate the cancer cells within a short time.

Hereinafter, the present invention will be described in detail with reference to examples. It is to be understood, however, that these examples are illustrative purposes and are not intended to limit the scope of the present invention.

Test Method (1) Drugs for Administration

The anticancer composition of the present invention, which was used in this test, was prepared as a formulation for local administration which would be injected directly into cancer cells. Specifically, hydroxychloroquine was added to physiological saline for injection at a concentration of 20% (w/v), and 20% ethanol as a solvent was added thereto in an amount of 10-20% based on the volume of the resulting composition. The mixture was dissolved by heating on a water bath. Then, lidocaine and riboflavin were added thereto in amounts of 2% (w/v) and 0.1% (w/v), respectively, thereby preparing an injectable composition for local administration.

Cisplatin used as a positive control drug was purchased from Sigma Co. (USA).

(2) Cancer Cell Line

The cancer cell line used in this Example was Sarcoma-180 (KCLB 4066) obtained from the Korean Cell Line Bank.

As a culture medium for the cell line, RPMI 1640 medium containing 10% fetal bovine serum (FBS) was used, which was supplemented with streptomycin (100 µl/ml) and penicillin (100 µl/ml).

The Sarcoma-180 cell line was subcultured in a 5% $CO_2$ incubator at 37° C. for 48 hours and used in the test.

For animal tests, the Sarcoma-180 cell line was injected into the abdominal cavity of ICR mice at a concentration of $2\times10^7$ cells/ml. After about 2 weeks, the ascites was collected and centrifuged at 2000 rpm, and the precipitate was washed twice and then stained with 0.4% trypsin blue, thereby obtaining $2\times10^7$ cells/ml.

(3) Test Animals 5-week-old ICR mice were purchased and acclimated for 1 week before use in the test. The animals were housed at a temperature of 22±2° C. and a relative humidity of 50% under a 12-hr light/12-hr dark cycle.

TEST EXAMPLE 1

Measurement of Cytotoxicity Against Sarcoma 180

In order to evaluate the effect of the composition of the present invention on cytotoxicity, an MTT assay was used. The MTT assay is a laboratory test method for measuring cell viability and can be regarded as a standard colorimetric assay. The MTT assay capable of accurately measuring the proliferation and the number of living cells is an essential technique in the bioscience field, particularly the tumor biology field.

Before in vivo tests such as animal tests are carried out in order to search effects for the development of novel anticancer drugs or examine the sensitivity of existing anticancer drugs, a process of objectively demonstrating that the drugs inhibits the growth of tumors ex vivo should be carried out.

The sarcoma-180 cell line diluted to a cell concentration of $1\times10^5$ cells/ml was added to each well of a 96-well plate and cultured in a 5% $CO_2$ incubator at 37° C. for 24 hours. After 24 hours of the culture, the inventive composition diluted to 8 concentrations ranging from 1.0 µl to 0 µl was added to each well. Meanwhile, cisplatin was also diluted in the same manner as above and added to each well.

Then, the cells were cultured in a 5% $CO_2$ incubator at 37° C. for 24 hours, and 50 µl of MTT reagent was added thereto at a concentration of 2 mg/ml. Then, the cells were incubated in an incubator at 37° C. for 4 hours.

The cell culture was centrifuged to remove the supernatant, and 200 µl of DMSO was added to each well to dissolve the MTT-stained precipitate, after the $OD_{540}$ value at a wavelength of 540 nm was measured with an ELISA reader.

The 50% inhibitory concentration ($IC_{50}$) was defined as the drug concentration that resulted in 50% of cell viability, and the $IC_{50}$ value was used as an index of the anticancer effect of the drug.

FIG. 1 is a graphic diagram showing the results of evaluating the effect of the composition of the present invention on the growth of the sarcoma-180 cell line in comparison with a control drug by an MTT assay.

The composition of the present invention was added to the sarcoma-180 cell line suspension having a cell concentration of $2\times10^7$ cells/me, and then the anticancer activity thereof was compared with the control drug cisplatin. As a result, as can be seen in FIG. 1, the $IC_{50}$ value of the composition of the present invention was shown at 0.01 µl or less.

In other words, the $IC_{50}$ value of the inventive composition against sarcoma-180, determined by the MTT assay in vitro, was about 10 times lower than that of cisplatin, suggesting that the composition of the present invention has an excellent cytotoxic effect.

TEST EXAMPLE 2

Inhibitory Effect on Differentiation of Cancer Cells

In order to observe the anticancer activity of the composition of the present invention in ICR mice, the ICR mice were inoculated with Sarcoma-180 cells, and the effect of the composition of the present invention on the differentiation of Sarcoma-180 cells was evaluated.

Specifically, as shown in Table 1 below, animals acclimated to housing facilities were divided into a total of 6 groups (G1 to G6), each consisting of 12 animals. Table 1 shows the establishment of test groups and the drug concentration.

TABLE 1

| | Group | Dose | Number of animals |
|---|---|---|---|
| G1 | N (normal group) | 0 | 12 |
| G2 | C (control group) | 0 | 12 |
| G3 | L (low-dose group) | 16.6 µl/kg weight | 12 |
| G4 | M (middle-dose group) | 83.3 µl/kg weight | 12 |
| G5 | H (high-dose group) | 166.6 µl/kg weight | 12 |
| G6 | Cis (cisplatin) | 20 mg/m² | 12 |

A sarcoma-180 cell suspension having a cell concentration of $2\times10^7$ cells/ml was transplanted by subcutaneous injection into the inguinal region of all the groups excluding the normal group, thereby inducing solid cancer. The composition of the present invention was set at low dose (16.6 µl/kg weight), medium dose (83.3 µl/kg weight) and high dose (166.6 µl/kg weight), and each dose of the composition was administered into the mice at 3-day intervals for 6 weeks from the time point immediately after inducing ascites cancer, while the effects of the inventive composition on the implantation and differentiation of the cancer cell line were evaluated and compared with those of cisplatin.

On the final day of the test, the animals were biopsied, and the number of animals in which sarcoma-180 cells stably grew was measured and used as an anticancer index. The same test was carried out twice, and the two measurements were averaged.

Figure 2:
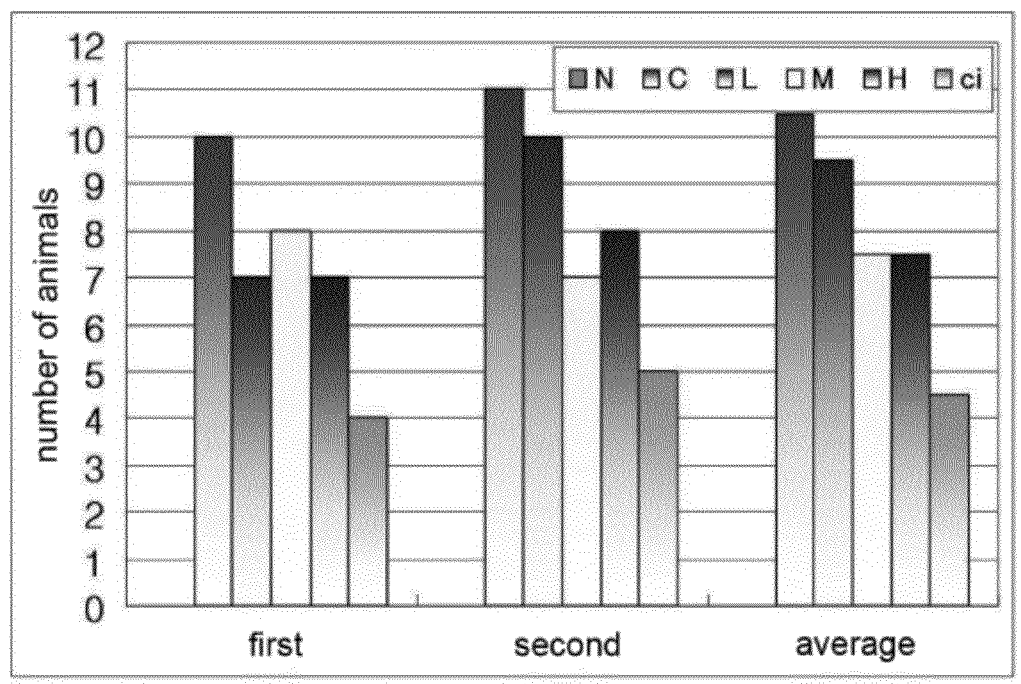
FIG. 2 is a graphic diagram showing the effect of the composition of the present invention on the differentiation of the sarcoma-180 cell line in ICR mice in comparison with a control drug.

FIG. 2 is a graphic diagram showing the effect of the composition of the present invention on the differentiation of the sarcoma-180 cell line in ICR mice in comparison with a control drug. In FIG. 2, L: low dose of the inventive composition; M: meddle dose of the inventive composition; H: high dose of the inventive composition; cis: cisplatin; N: normal group; and C: control group.

As described above, after completion of the test, the presence or absence of cancer cells in the inguinal region was observed by biopsy. As a result, as can be seen in FIG. 2, cancer cells were observed in 9.5 animals for the low-dose group, 7.5 animals for the middle-dose and high-dose groups, and 4.5 animals for the control drug cisplatin.

In other words, the inhibitory effect of the composition of the present invention on the differentiation of cancer cells was slightly higher than that of the control group, but was not higher than that of cisplatin.

It is believed that the reason why the effectiveness of the composition of the present invention was different between in vivo and in vitro is because the diffusion length of hydroxychloroquine was limited because hydroxychloroquine is insoluble at room temperature.

TEST EXAMPLE 3

Anticancer Effect on Solid Cancer

In order to observe the anticancer activity of the composition of the present invention in ICR mice, the ICR mice were inoculated with sarcoma-180 cells to induce solid cancer, after which the effect of the inventive composition on the death of sarcoma-180 cells was evaluated.

According to Table 2 below, animals acclimated to housing facilities were divided into a total of 4 groups (G1 to G4), each consisting of 10 animals. Table 2 below shows the establishment of test groups and the drug concentration.

TABLE 2

| | Group | Dose | Number of animals |
|---|---|---|---|
| G1 | Control group | 0 | 10 |
| G2 | Low-dose group | 83 µl/kg weight | 10 |
| G3 | Middle-dose group | 166 µl/kg weight | 10 |
| G4 | High-dose group | 415 µl/kg weight | 10 |

A sarcoma-180 cell suspension having a cell concentration of $2\times10^7$ cells/ml was transplanted by subcutaneous injection into the inguinal region of all the groups, thereby inducing solid cancer. The composition of the present invention was set at the doses shown in Table 2, and each dose of the composition was administered into the mice twice a week at 3-day intervals for 6 weeks from 1 week after transplanting the cancer cell line, while the degree of induction of solid cancer was observed.

On the final day of the test, visual observation was carried out by biopsy and the weight of tumor cells was measured and used as an anticancer index.

Figure 3:
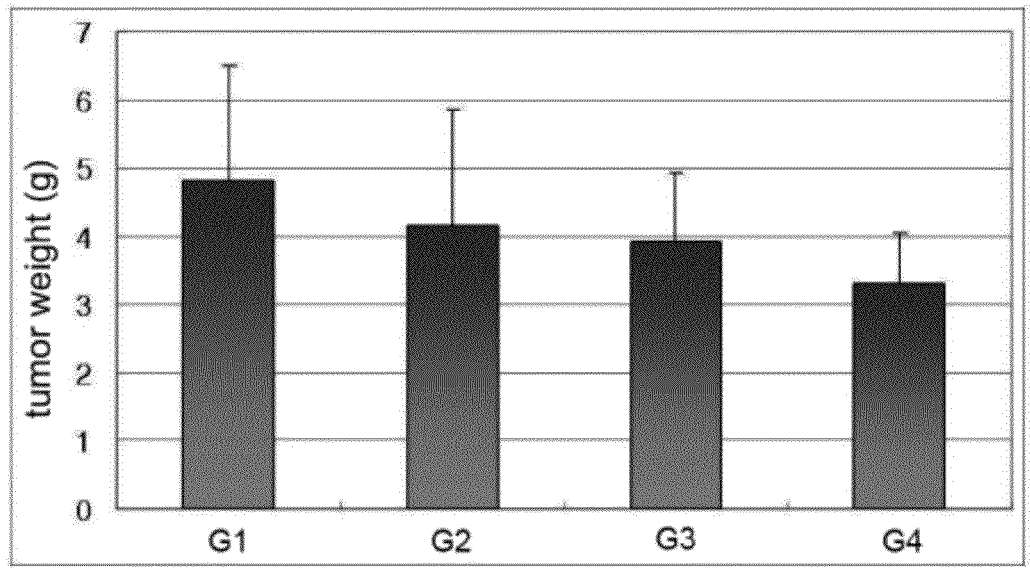
FIG. 3 is a graphic diagram showing the effect of the composition of the present invention on the growth of solid cancer induced by sarcoma-180 cells in ICR mice.

FIG. 3 is a graphic diagram showing the effect of the composition of the present invention on the growth of solid cancer induced by sarcoma-180 cells in ICR mice. In FIG. 3, G1: control group; G2: administered with 83 µl/kg weight of the inventive composition (20% hydroxychloroquine); G3: administered with 166 µl/kg weight of the inventive composition; and G4: administered with 415 µl/kg weight of the inventive composition.

As a result, as can be seen in FIG. 3, the average weight of tumor cells was 4.81±1.69 g for the control group not administered with the drug, whereas it was 4.16±1.68 g for the G2 group (administered with the inventive composition (20% hydroxychloroquine), 3.92±1.00 g for the G3 group, and 3.31±0.72 g for the G4 group, suggesting that the composition of the present invention reduced the weight of solid cancer in a dose-dependent manner.

TEST EXAMPLE 4

Observation Anticancer Effect on Ascites Cancer

In mice having ascites cancer induced by transplantation of Sarcoma-180 cells, the anticancer effect of the composition of the present invention and the effect of the composition on the extension of the life span of the mice were evaluated.

According to Table 3 below, animals acclimated to housing facilities were divided into a total of 3 groups (G1 to G3), each consisting of 10 animals. Table 3 below shows the establishment of test groups and the drug concentration.

TABLE 3

| | Group | Dose | Number of animals |
|---|---|---|---|
| G1 | Control group | 0 | 10 |
| G2 | Middle-dose group | 166 µl/kg weight | 10 |
| G3 | High-dose group | 830 µl/kg weight | 10 |

A sarcoma-180 cell suspension having a cell concentration of $2\times10^7$ cells/ml was inoculated into the abdominal cavity of all the group to induce ascites cancer. The composition of the present invention was set at the doses shown in Table 3, and each dose of the composition was administered into the animals at 3-day intervals for 6 weeks after inducing the ascites cancer, while the mortality of the animals was observed and compared with that in the group administered with cisplatin.

Figure 4:
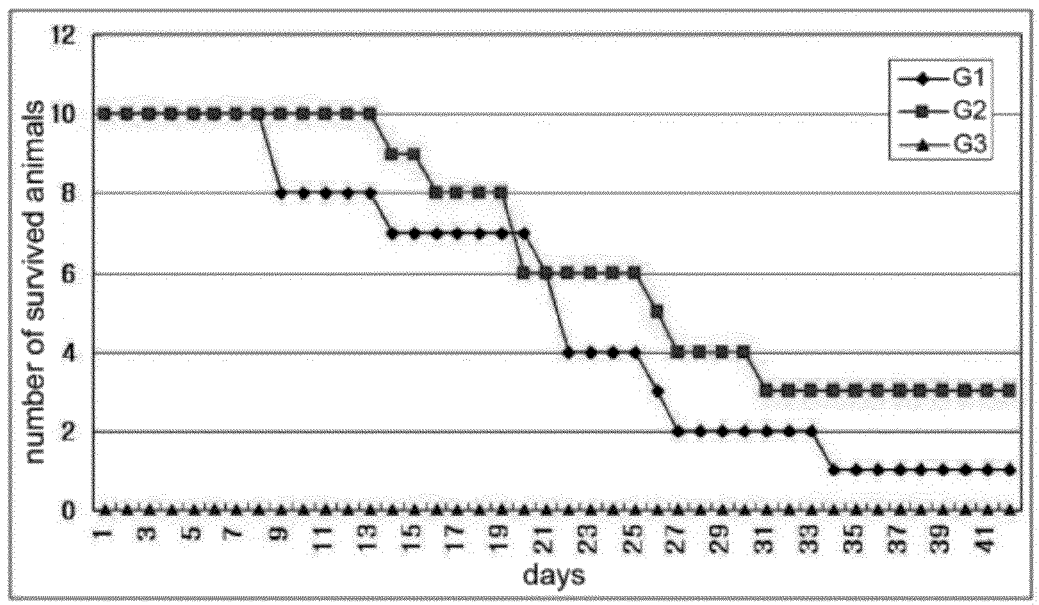
FIG. 4 is a graphic diagram showing the effect of the composition of the present invention on the extension of the life span of ICR mice after inducting ascites carcinoma in the ICR mice by sarcoma-180 cells.

FIG. 4 is a graphic diagram showing the effect of the composition of the present invention on the extension of the life span of ICR mice after inducting ascites cancer in the ICR mice by sarcoma-180 cells. In FIG. 4, G1: control group; G2: administered with 166 µl/kg weight of the inventive composition (20% hydroxychloroquine); and G3: administered of 830 µl/kg weight of the inventive composition.

The mortality of the animals by ascites cancer was examined until the final day (day 42) of the test. As a result, in the control group, dead animals started to appear from day 9, and on day 21, about half of the animals were dead, and on day 42, one animal survived, but it is believed that the survived animal is an animal in which ascites cancer was not induced or the degree of induction of ascites cancer was insufficient. In the G2 group, dead animals started to appear on day 13 slightly later than the case of the control group, and on day 26, half of the animals were dead, but at the final day of the test, 3 animals survived. However, in the G3 group, all the animals were dead on the first day of administration of the drug. These results suggest that the composition of the present invention contributes to the extension of the life span of animals having ascites cancer.

As described above, the injectable composition for local administration comprising hydroxychloroquine according to the present invention shows an $IC_{50}$ value against sarcoma-180 cells, which is about 10 times lower than cisplatin, as determined by the MTT assay in vitro, suggesting that the composition of the present invention has an excellent cytotoxic effect. Also, the composition of the present invention shows dose-dependent effects against solid cancer induced by sarcoma-80 cells in vivo. In addition, the composition of the present invention has the effect of extending the life expectancy of patients having ascites cancer induced by sarcoma-80 cells.

The invention claimed is:

1. An injectable anticancer composition for local administration comprising hydroxychloroquine or its salt, wherein the content of hydroxychloroquine in the composition is 20-25% (w/v).

2. The anticancer composition of claim 1, wherein the composition is to be injected directly into cancer cells.

3. The anticancer composition of claim 1 or 2, wherein the salt of hydroxychloroquine is a sulfate of hydroxychloroquine.

4. The anticancer composition of claim 1, wherein the content of hydroxychloroquine in the composition is 20% (w/v).

5. The anticancer composition of claim 1 or 2, wherein the composition further comprises a local anesthetic and an antioxidant.

6. The anticancer composition of claim 5, wherein the local anesthetic is lidocaine which is contained at a concentration of 1-2% (w/v), and the antioxidant is riboflavin which is contained at a concentration of 0.1-0.5% (w/v).

7. A method for treating cancer, comprising:
preparing an injectable anticancer composition for local administration, the composition comprising 20-25% (w/v) hydroxychloroquine or its salt; and
injecting the composition directly into cancer cells.

8. The method of claim 7, wherein the salt of hydroxychloroquine is a sulfate of hydroxychloroquine.

9. The method of claim 7, wherein the content of hydroxychloroquine in the composition is 20% (w/v).

10. The method of claim 7, wherein the composition further comprises a local anesthetic and an antioxidant.

11. The method of claim 10, wherein the local anesthetic is lidocaine which is contained at a concentration of 1-2% (w/v), and the antioxidant is riboflavin which is contained at a concentration of 0.1-0.5% (w/v).

* * * * *